United States Patent
Coles, Jr. et al.

(10) Patent No.: US 9,993,631 B2
(45) Date of Patent: Jun. 12, 2018

(54) VENTRICULOPERITONEAL SHUNT WITH PRESSURE RESPONSIVE ELEMENT

(71) Applicant: The Johns Hopkins University, Baltimore, MD (US)

(72) Inventors: George L. Coles, Jr., Baltimore, MD (US); Sybil Klaus, Baltimore, MD (US); Eric Jackson, Baltimore, MD (US); Philippe M. Burlina, North Bethesda, MD (US); Richard S. Potember, Ellicott City, MD (US); Wayne I. Sternberger, Highland, MD (US); John H. Benson, Ellicott City, MD (US); Benjamin Elder, Perry Hall, MD (US)

(73) Assignee: The Johns Hopkins University, Baltimore, MD (US)

( * ) Notice: Subject to any disclaimer, the term of this patent is extended or adjusted under 35 U.S.C. 154(b) by 457 days.

(21) Appl. No.: 14/855,534

(22) Filed: Sep. 16, 2015

(65) Prior Publication Data
US 2016/0074638 A1    Mar. 17, 2016

Related U.S. Application Data

(60) Provisional application No. 62/051,371, filed on Sep. 17, 2014.

(51) Int. Cl.
*A61M 27/00*    (2006.01)

(52) U.S. Cl.
CPC ................. *A61M 27/006* (2013.01)

(58) Field of Classification Search
CPC .................................. A61M 27/006
See application file for complete search history.

(56) References Cited

U.S. PATENT DOCUMENTS

| | | | |
|---|---|---|---|
| 6,610,016 B1 * | 8/2003 | Violante | A61B 8/481 600/458 |
| 2008/0195198 A1 * | 8/2008 | Asgari | A61L 31/022 623/1.49 |

* cited by examiner

*Primary Examiner* — Leslie Deak
(74) *Attorney, Agent, or Firm* — Noah J. Hayward

(57) ABSTRACT

A ventriculoperitoneal shunt includes a proximal catheter, a distal catheter, a shunt valve operably coupling the proximal catheter to the distal catheter, and a contrast container containing contrast material configured to change acoustic impedance proportionally to a change in pressure applied to the contrast container.

11 Claims, 7 Drawing Sheets

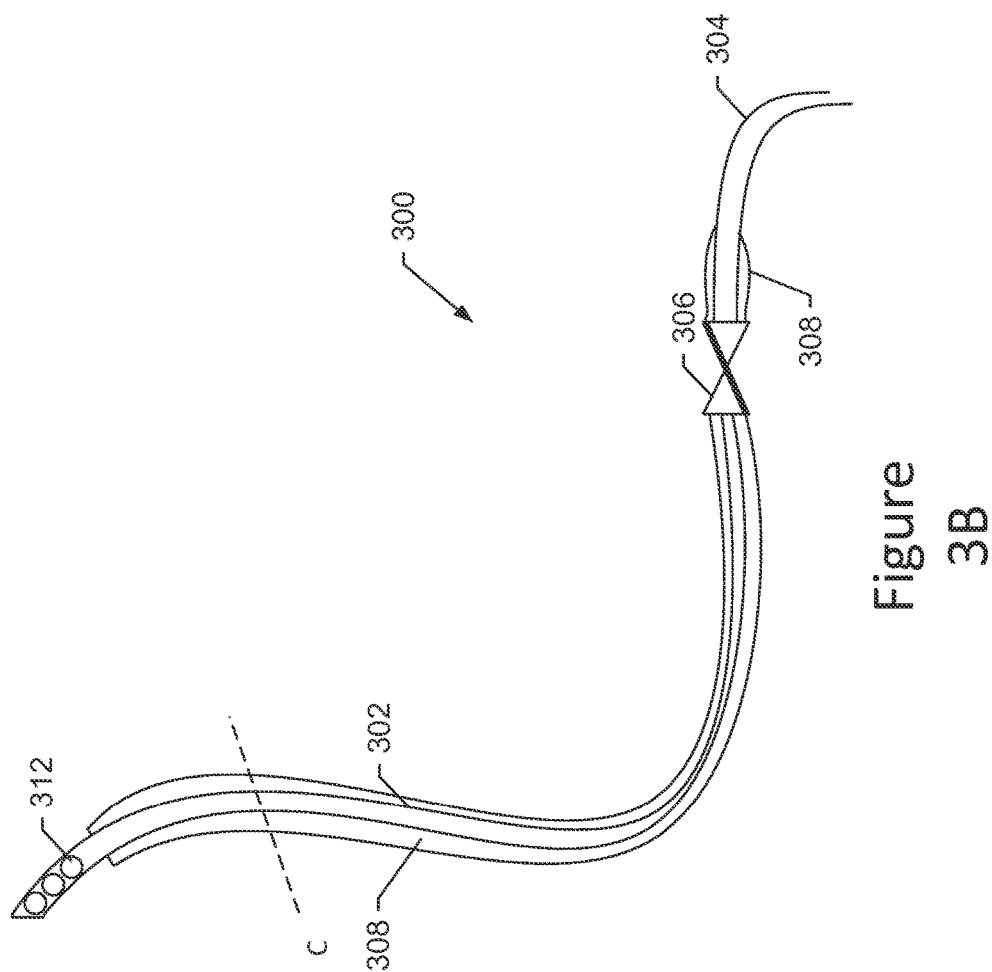

VENTRICULOPERITONEAL SHUNT WITH PRESSURE RESPONSIVE ELEMENT

CROSS REFERENCE TO RELATED APPLICATIONS

This application claims the benefit of U.S. Provisional Application No. 62/051,371 filed on Sep. 17, 2014, the entire contents of which are hereby incorporated herein by reference.

TECHNICAL FIELD

Example embodiments generally relate to a ventriculoperitoneal shunt and, in particular, relate to a ventriculoperitoneal shunt with a pressure responsive element.

BACKGROUND

A ventriculoperitoneal (VP) shunt is used in Hydrocephalus cases to drain excess cerebral spinal fluid (CSF) from the ventricles to reduce the pressure in the ventricular cavity. Some VP shunts may be equipped with an adjustable or programmable shunt valve configured to open and drain excess CSF in an instance in which a predetermined pressure set point is reached within the ventricular cavity.

In some cases, the VP shunt may become blocked or clogged preventing pressure relief in the ventricular cavity; however, the symptoms of a blocked VP shunt and the symptoms of nasal congestion, typical of a common cold, may be substantially similar. A ventricular pressure measurement is used to differentiate between nasal congestion and blockage of the VP shunt. In some cases, invasive procedures such as drilling a hole in the skull are used to take a ventricular pressure measurement. In other instances, computerized axial tomography (CT) scans or X-rays may be taken over a period of several days and changes in the CT or X-ray images may be indicative of a ventricular pressure change. In still another instances, an ultrasound of the retinal vessel may be used for indirect measurement of ventricular pressure. As such, there is no non-invasive method to quickly and directly measure ventricular pressure.

BRIEF SUMMARY

Accordingly, example embodiments provide, among other things, a ventriculoperitoneal shunt with a pressure responsive element, as described below. In one example embodiment, a ventriculoperitoneal shunt is provided including a proximal catheter, a distal catheter, a shunt valve operably coupling the proximal catheter to the distal catheter, and a contrast container containing contrast material configured to change acoustic impedance proportionally to a change in pressure applied to the contrast container.

In another example embodiment, a ventriculoperitoneal shunt is provided including a proximal catheter, a distal catheter, and a shunt valve operably coupling the proximal catheter to the distal catheter. A surface of at least a portion of the proximal catheter is roughened to be hydrophobic.

In yet another example embodiment, a ventriculoperitoneal shunt is provided including a proximal catheter, a distal catheter, a shunt valve operably coupling the proximal catheter to the distal catheter, and a contrast container containing contrast material configured to change acoustic impedance proportionally to a change in pressure applied to the contrast container. The contrast container is operably coupled to the end of the proximal catheter opposite the shunt valve and the contrast material comprises a plurality of microbubbles and the change in acoustic impedance is caused by a change in the diameter of the plurality of microbubbles

BRIEF DESCRIPTION OF THE SEVERAL VIEWS OF THE DRAWING(S)

Having thus described the VP shunt in general terms, reference will now be made to the accompanying drawings, which are not necessarily drawn to scale, and wherein:

FIGS. 3A and 3B illustrate example VP shunts according to an example embodiment;

DETAILED DESCRIPTION

Figure 1:
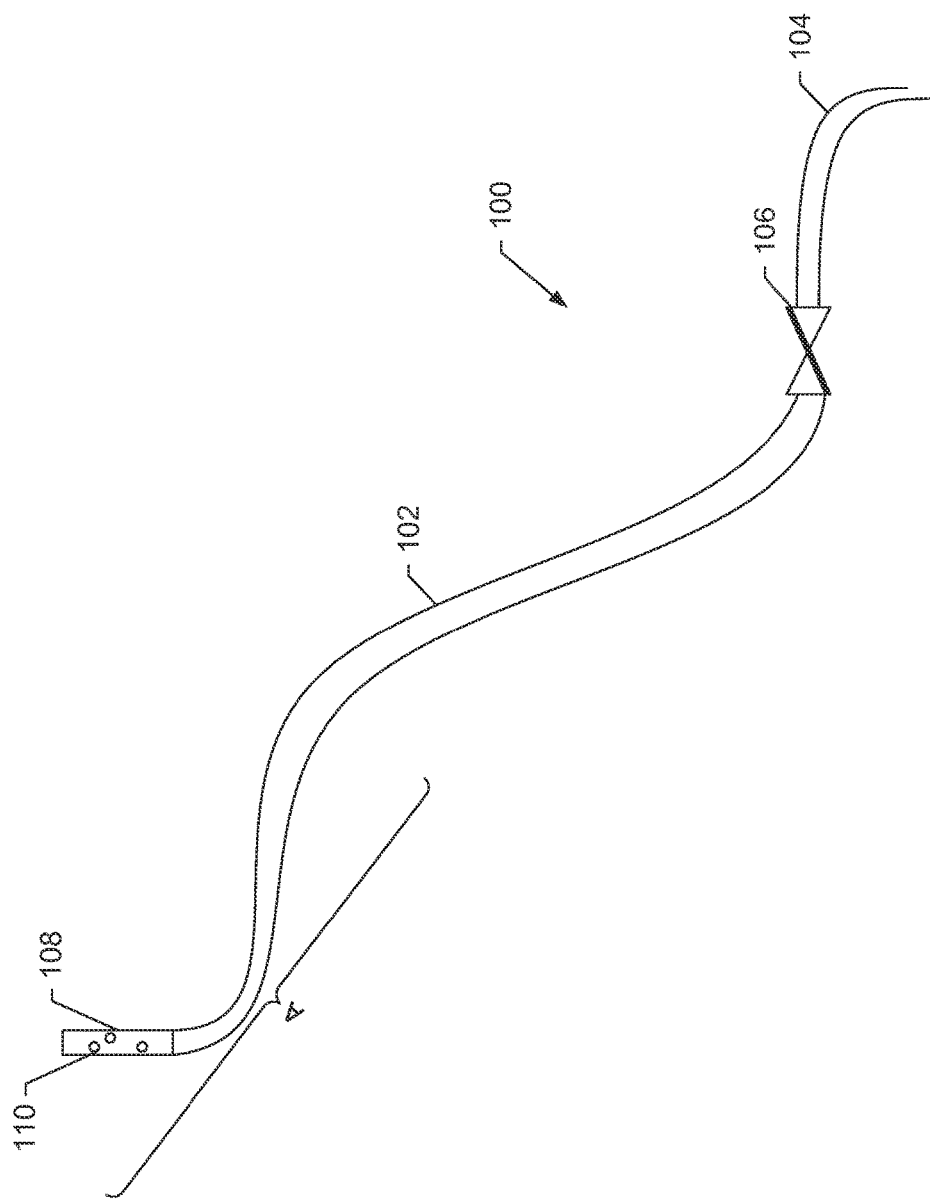
FIG. 1 illustrates an example VP shunt with a contrast container according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. As used herein, operable coupling should be understood to relate to direct or indirect connection that, in either case, enables functional interconnection of components that are operably coupled to each other.

In an example embodiment, the VP shunt includes a pressure responsive element, such as a contrast container, operably coupled to the proximal catheter. The contrast container may be inserted into the ventricular cavity of a patient with the proximal catheter. An ultrasound may be taken to establish a base line acoustic impedance of the contrast container. In an instance in which the ventricular pressure needs to be determined, such as distinguishing between nasal cavity pressure and intracranial pressure of the ventricular cavity, an ultrasound, or other sonic imaging, of the contrast container may be performed to determine a measured acoustic impedance. A measured pressure may be determined by comparing the baseline acoustic impedance to the measured acoustic impedance, without performing an invasive procedure. Since the determination of the ventricular pressure may be determined without an invasive procedure, there is no recovery time, little to no procedural risk, and no risk of secondary infections due to the procedure.

In some instances, the contrast container may be operably coupled to the proximal catheter at a ventricular end opposite the shunt valve. In an instance in which the contrast container is operably coupled at the ventricular end of the proximal catheter, a cranial ultrasound or other sonic imaging, may be used to determine the acoustic impedance of the contrast container.

In some instances the contrast container may be dispose in parallel with or within the proximal catheter. In an instance in which the contrast container is disposed in parallel with or within the proximal catheter, an ultrasound, or other sonic imaging, of the contrast container may be performed in the area in which the proximal catheter traverses the patient's clavicle. Performing the ultrasound at the traverse of the clavicle may be beneficial since the ultrasound may only need to be transmitted through skin and a thin layer of fat, providing a clearer ultrasound image than other areas of the body.

In an example embodiment, a portion of the surface of the proximal catheter may be roughened causing the surface to be hydrophobic. The roughening of the surface may include spikes which inhibit attachment of macrophages and/or choroid plexus cells, which may block or limit flow of the VP shunt.

In some example embodiments, a drug eluting coating may be disposed on at least a portion of the proximal catheter. The drug eluting coating, such as an anti-inflammatory drug, may reduce inflammation of tissues around the ventricular shunt, which may in turn inhibit immune system response, such as macrophage production.

Example VP Shunt with Contrast Container

An example embodiment of the VP shunt will now be described in reference to FIG. 1, which illustrates an example VP shunt 100 with a contrast container 108 according to an example embodiment. The VP shunt may include a proximal catheter 102, a distal catheter 104 and a shunt valve 106.

The proximal catheter 102 may be inserted into the ventricular cavity of a patient. The shunt valve 106 may be adjusted or programmed to relieve pressure at a predetermined ventricular pressure set point, such as 20, 50, 100, 150, 200 mm $H_2O$, or the like. The distal catheter 104 may be inserted into the chest or abdominal cavity of the patient. In an instance in which the pressure of the ventricular cavity reaches the predetermined ventricular pressure setpoint, the shunt valve 106 may open allowing excess CSF to flow from the ventricular cavity, into the proximal catheter 102, through shunt valve 106, through the distal catheter 104, and into the chest or abdominal cavity.

The contrast container 108, e.g., the pressure responsive element, may be a flexible polymer configured to transfer a pressure applied to the surface of the contrast container 108 to a contrast solution, such as deionized water, saline solution, or the like, within the contrast container 108. The contrast container 108 may include contrast material configured to suspend microbubbles 110 in the contrast solution. In an example embodiment, the microbubbles 110 may be 2-15 microns in diameter. The contrast material may include a protein extracted hydrophobin (such as produced by a filamentous fungi), a collagen foam, or the like, which may cause the microbubbles 110 to be stable for the lifetime of the VP shunt 100, for example 6 months, 8 months, 12 months, or the like.

The microbubbles 110 may change diameter based on a change in pressure applied to the contrast container 108 and transferred by the contrast material to the microbubbles 110. In an example embodiment, the microbubbles 110 may decrease in diameter in response to an increase in pressure applied to the contrast container 108. In an example embodiment, a decrease in diameter of the microbubbles 110 based on an increase of pressure applied to the contrast container may be asymptotic. In some example embodiments, the microbubbles 110 may change diameter proportionally to the change in pressure applied to the contrast container 108, in a service range, such as 0-400 mm $H_2O$.

A sonic imaging technique, such as ultrasound, Transcranial Doppler test (TDT), or the like may be used to determine an echo amplitude intensity or acoustic impedance of the contrast container 108. The acoustic impedance may be based on the size of the microbubbles 110. A baseline acoustic impedance may be determined at a known pressure, such as ambient pressure, or a measured pressure within the ventricular cavity.

The contrast container 108 may be operably coupled to a ventricular end of the proximal catheter 102 opposite the shunt valve 106 and inserted into the ventricular cavity with the ventricular end of the proximal catheter 102. The ventricular end (A) of the proximal catheter 102 is depicted in further detail in FIG. 2.

A sonic image, such as an ultrasound, TDT, or the like may be used to determine an echo amplitude intensity or acoustic impedance of the contrast container 108 at a second time, such as to verify operation, e.g. flow, of the VP shunt 100. A measured pressure associated with the contrast container 108, e.g. ventricular pressure, may be determined based on the difference between the baseline echo amplitude intensity or acoustic amplitude and the measured echo amplitude intensity or acoustic amplitude. In an example embodiment, the echo amplitude intensity or acoustic amplitude may be proportional to the pressure applied to the contrast container 108.

In an alternative embodiment, the pressure responsive element may be a cylindrical container substantially similar to the contrast container 108, which is filled with an inert gas, such as Nitrogen or Argon, a low viscosity fluid, such as deionized water, or the like. A baseline imaging may be used to determine a baseline diameter of the cylindrical container. A subsequent imaging may be used to determine a measured pressure based on the change in diameter of the cylindrical container. The diameter of the cylindrical container may change based on a change in the pressure applied to the external surface of the cylindrical container.

Example Ventricular End of a Proximal Catheter

Figure 2:
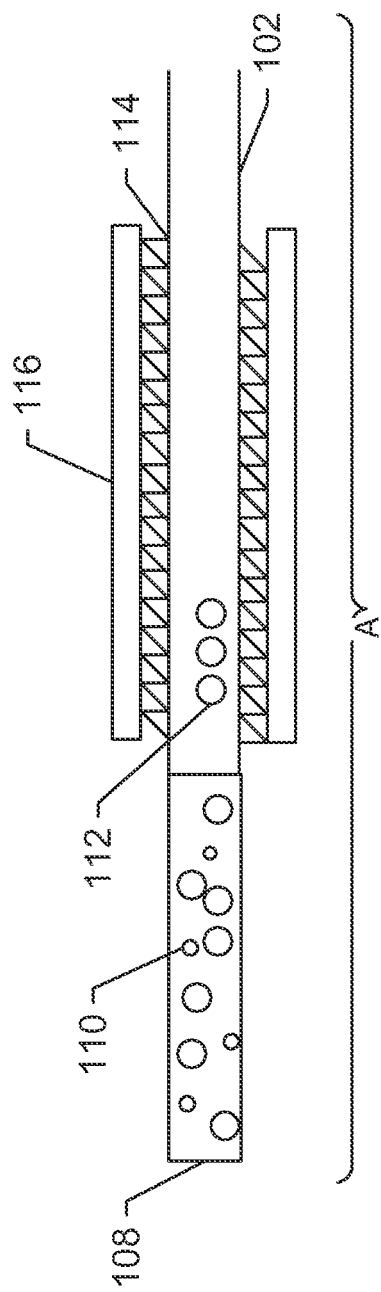
FIG. 2 illustrates a ventricular end of a proximal catheter according to an example embodiment.

FIG. 2 illustrates an example ventricular end (A) of a proximal catheter 102 according to an example embodiment. The contrast container 108 may be operably coupled to the ventricular end of the proximal catheter 102. The operable coupling of the contrast container 108 to the ventricular end of the proximal catheter 102 may be plastic welding, solvent welding, or the like. The ventricular end of the contrast container 108 may be rounded to prevent or limit damage to tissue as the proximal catheter 102 is inserted into the ventricular cavity.

One or more drain apertures 112 may be disposed at or near the ventricular end of the proximal catheter 102 to allow for draining of fluid, such as CSF from the ventricular cavity.

In an example embodiment, the exterior surface of the ventricular end of the proximal catheter 102 may be roughened, such as by plasma roughening. The roughened surface 114 may cause the ventricular end of the proximal catheter 102 to be hydrophobic. The roughened surface 114 may include spikes with lengths of about 1-10 microns. The roughened surface 114 may be beneficial in inhibiting attachment of macrophages and/or choroid plexus cells, which may block or limit flow of the VP shunt 100.

Additionally or alternatively, the ventricular end of the proximal catheter 102 may include a drug eluting coating 116. The drug eluting coating 116 may include an anti-inflammatory agent or medication. The drug eluting coating 116 may extend the length of the proximal catheter 102 which is configured to be inserted into the patient. The drug eluting coating 116 may be beneficial in inhibiting immune system response to the proximal catheter 102, such as macrophage production.

Figure 3A:
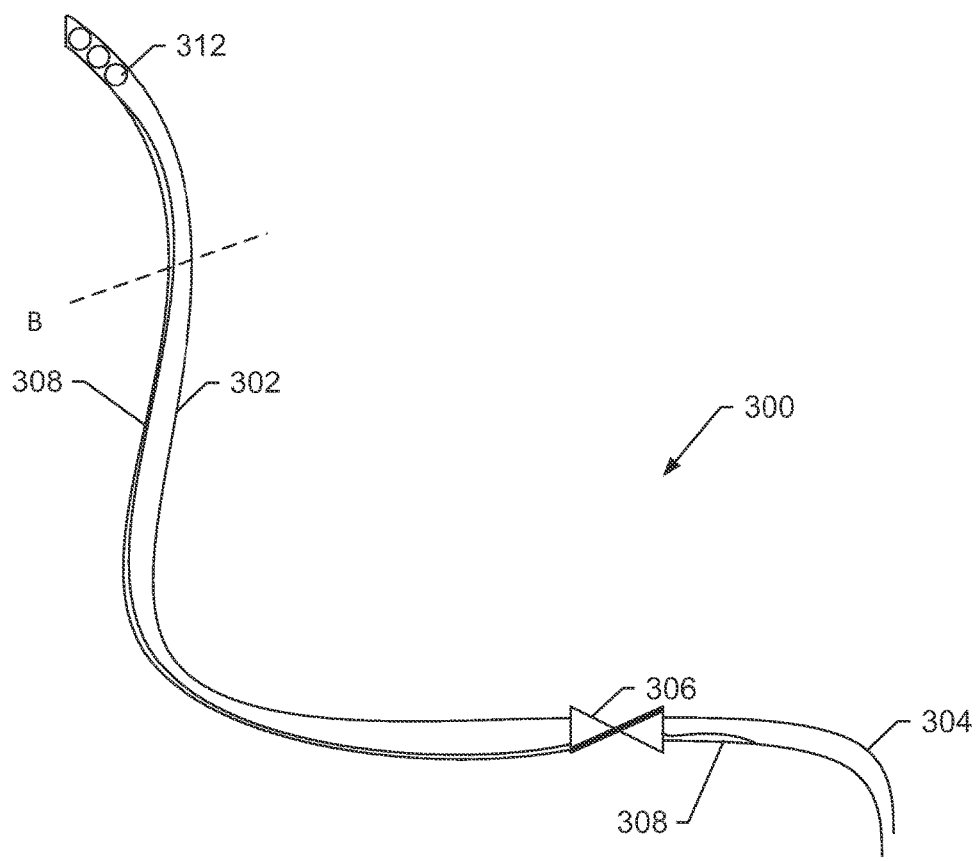

FIGS. 3A and 3B illustrate example VP shunts according to an example embodiment. In an example embodiment, the VP shunt 300 may include a proximal catheter 302, a distal catheter 304, and a shunt valve 306. The shunt valve 306 may operably couple the proximal catheter 302 to the distal catheter 304. One or more drain apertures 312 may be disposed at a ventricular end of the proximal catheter 302 opposite the shunt valve 306.

A contrast container 308 may be operably coupled to the proximal catheter 302. In an example embodiment, the contrast container 308 may be disposed in parallel with the proximal catheter 302. In an example embodiment, the contrast container 308 may be operably coupled to the exterior surface of the proximal catheter 302. In some embodiments, the contrast container 308 may be operably coupled within the proximal catheter 302, as depicted in cross section B of FIG. 4A. In an example embodiment, the contrast container 308 and proximal catheter 302 may be concentric circular tubes, as depicted in cross section C of FIG. 4B In an example embodiment, the contrast container 308 and proximal catheter 302 may be formed by creating a longitudinal seam in a lumen tube, such as a polymer tube, defining a first and second side of the tube. The first side, e.g. the contrast container 308, of the tube may be filled with the contrast material and contrast solution and may be sealed at both ends. The second side, e.g. the proximal catheter 302, may be left open at either end to allow for fluid translation.

In an example embodiment, the contrast container 308 may extend through shunt valve 306. The contrast container 308 may extend in parallel with the distal catheter 304, in a manner substantially similar to the extension of the contrast container with the proximal catheter as discussed above. The contrast container 803 may terminate a predetermined distance after the shunt valve 306, for example terminating at distance proximate to and after traversal of the clavicle of a patient.

In some examples, the contrast container 308 and proximal catheter 302 may be formed by common extrusion, such as a dual lumen tube. The contrast container 308 and the proximal catheter 302 may be extruded with a common wall.

Figure 4A:
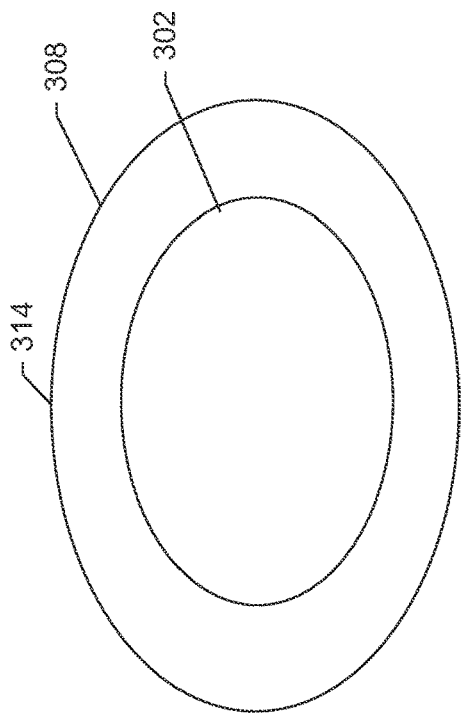
FIGS. 4A and 4B illustrate example cross sections of a VP shunts according to an example embodiment.
Figure 4B:
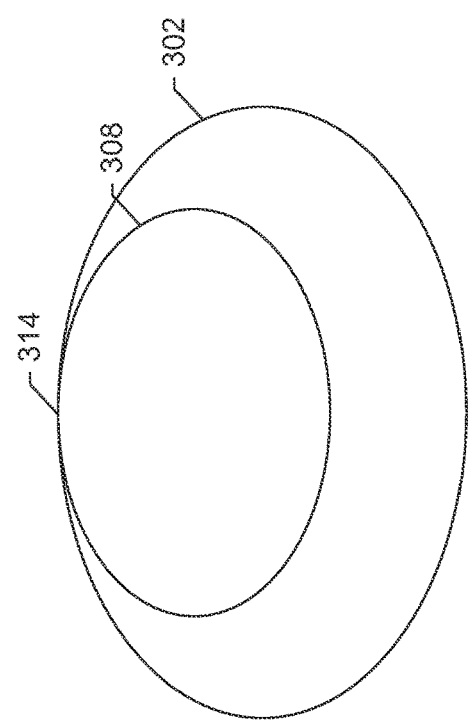

FIG. 4A illustrates an example cross section of a VP shunt 300 according to an example embodiment. The depicted cross section of FIG. 4A may be the cross section B depicted in FIG. 3A. In an example embodiment, the contrast container 308 may be disposed within the proximal catheter 302. In some example embodiments, the contrast container 308 and the proximal catheter 302 may include a common wall 314. In an alternative embodiment, depicted in FIG. 4B which may be the cross section C depicted in FIG. 3B, the proximal catheter 302 may be disposed within the contrast container 308, such as concentric circular tubes.

Figure 5:
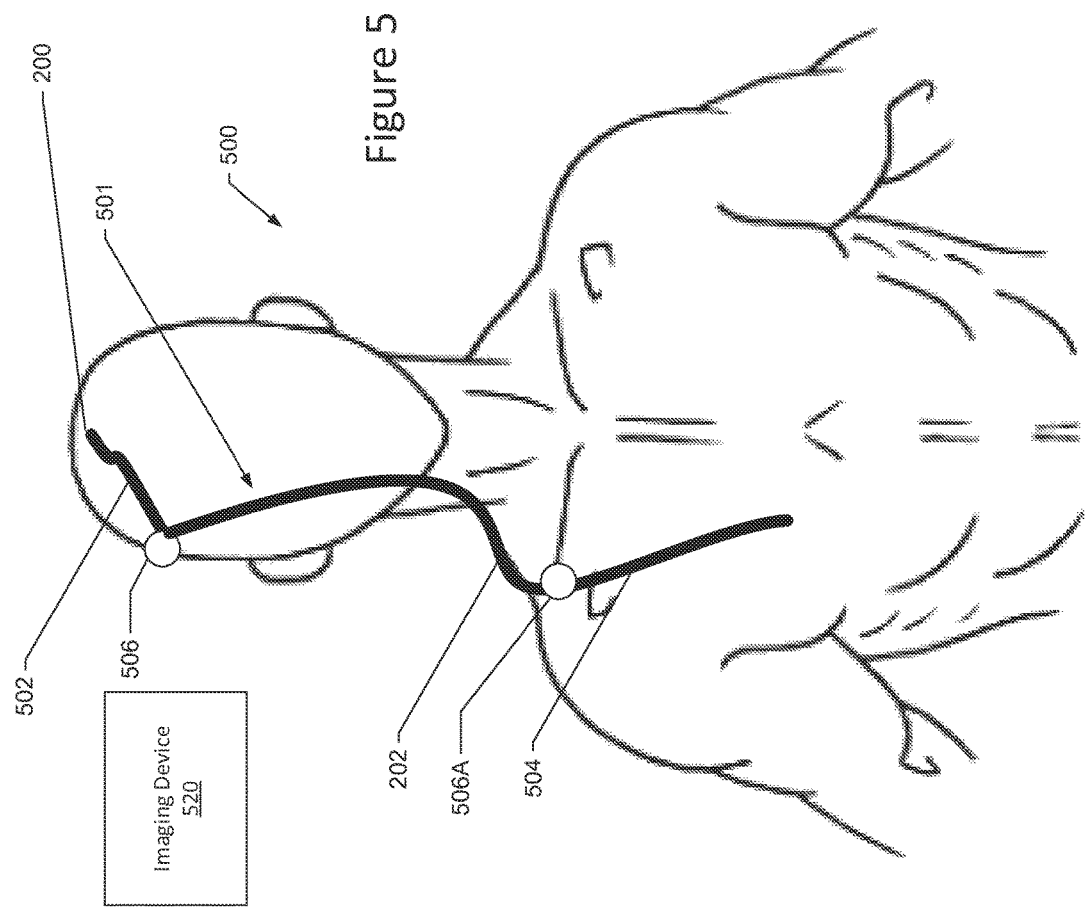
FIG. 5 illustrates a deployment of a VP shunt in a patient according to an example embodiment.

FIG. 5 illustrates a deployment of a VP shunt 501 in a patient 500 according to an example embodiment. The VP shunt 501 may include a proximal catheter 502 inserted into the ventricular cavity of the patient 500 and a distal catheter 504 inserted into a cavity of the patient 500, such as the chest or abdominal cavity.

In an example embodiment in which the contrast container, such as contrast container 108 is operably coupled to the ventricular end of the proximal catheter 502, an imaging device 520 may be used to perform the sonic imaging at cranial position 200 within the ventricular cavity. In an instance in which the contrast container is operably coupled to the ventricular end of the proximal catheter, the shunt valve may be positioned at the side of the cranium.

In an example embodiment in which the contrast container, such as contrast container 308 is operably coupled and disposed in parallel with the proximal catheter 302, the imaging device 520 may be used to perform the sonic imaging at a location at which the proximal catheter 302 is close to the surface of the body, such as where the proximal catheter 502 traverses a clavicle of the patient 500.

Method for Determining a Ventricular Pressure

Figure 6:
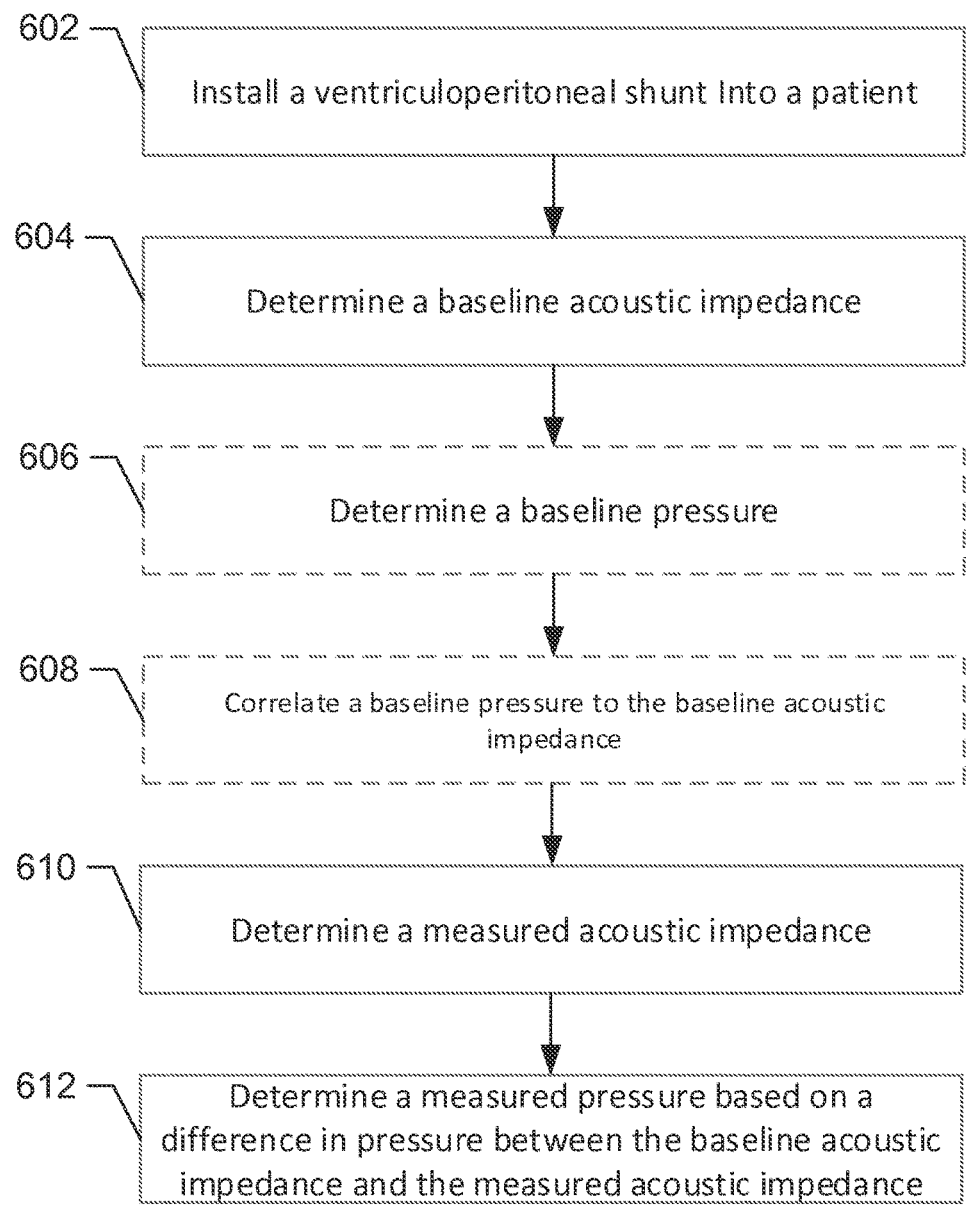
FIG. 6 illustrates an example flowchart of a method of determining a ventricular pressure according to an example embodiment.

FIG. 6 illustrates an example flowchart of a method of determining a ventricular pressure according to an example embodiment. The method may include, at operation 602, installing a VP shunt into a patient. At operation 604, the method may include determining a baseline acoustic impedance. The method may include determining a measured acoustic impedance, at operation 610, and determining a measured pressure based on the difference between the baseline acoustic impedance and the measured acoustic impedance, at operation 612.

In an example embodiment, the method may optionally include, as denoted by the dashed box, operation 606, determining a baseline pressure. The method may also optionally include correlating a baseline pressure to the baseline acoustic impedance, at operation 608.

In some embodiments, the VP shunt may be further configured for optional modifications. In this regard, for example, the contrast material may include a plurality of microbubbles and the change in acoustic impedance may be caused by a change in the diameter of the plurality of microbubbles. In an example embodiment, the contrast container is operably coupled to a ventricular end of the proximal catheter opposite the shunt valve. In some example embodiments, the contrast container is a tube disposed in parallel with the proximal catheter. In an example embodiment, the contrast container is disposed within the proximal catheter. In some example embodiments, a surface of at least a portion of the proximal catheter is roughened to be hydrophobic. In some example embodiments, the roughened surface includes a plurality of spikes of about 1-10 microns. In an example embodiment, a drug eluting coating is disposed on at least a portion of the proximal catheter. In some example embodiments, the drug eluting coating includes an anti-inflammatory medication.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A ventriculoperitoneal shunt comprising:
   a proximal catheter;
   a distal catheter;
   a shunt valve operably coupling the proximal catheter to the distal catheter; and
   a contrast container including a contrast material configured to change acoustic impedance proportionally to a change in pressure applied to the contrast container.

2. The ventriculoperitoneal shunt of claim 1, wherein the contrast material comprises a plurality of microbubbles and the change in acoustic impedance is caused by a change in a diameter of microbubbles of the plurality of microbubbles.

3. The ventriculoperitoneal shunt of claim 1, wherein the contrast container is operably coupled to a ventricular end of the proximal catheter opposite the shunt valve.

4. The ventriculoperitoneal shunt of claim 1, wherein the contrast container is a tube disposed in parallel with the proximal catheter.

5. The ventriculoperitoneal shunt of claim 1, wherein the contrast container is disposed within the proximal catheter.

6. The ventriculoperitoneal shunt of claim 1, wherein a surface of at least a portion of the proximal catheter is roughened to be hydrophobic.

7. The ventriculoperitoneal shunt of claim 1, wherein a drug eluting coating is disposed on at least a portion of the proximal catheter.

8. The ventriculoperitoneal shunt of claim 1, wherein the drug eluting coating comprises an anti-inflammatory medication.

9. A ventriculoperitoneal shunt comprising:
   a proximal catheter;
   a distal catheter;
   a shunt valve operably coupling the proximal catheter to the distal catheter; and
   a contrast container containing contrast material configured to change acoustic impedance proportionally to a change in pressure applied to the contrast container,
   wherein the contrast container is operably coupled to the end of the proximal catheter opposite the shunt valve and the contrast material comprises a plurality of microbubbles and the change in acoustic impedance is caused by a change in a diameter of bubbles of the plurality of microbubbles.

10. The ventriculoperitoneal shunt of claim 9, wherein a surface of at least a portion of the proximal catheter is roughened to be hydrophobic.

11. The ventriculoperitoneal shunt of claim 9, wherein a drug eluting coating comprising an anti-inflammatory medication is disposed on at least a portion of the proximal catheter.

* * * * *